(12) United States Patent
Chattopadhyay et al.

(10) Patent No.: US 7,901,606 B2
(45) Date of Patent: *Mar. 8, 2011

(54) PRODUCTION OF POROUS MATERIALS BY SUPERCRITICAL FLUID PROCESSING

(75) Inventors: Pratibhash Chattopadhyay, North Royalton, OH (US); Boris Y. Shekunov, Aurora, OH (US); Jeffrey S. Seitzinger, Broadview Heights, OH (US)

(73) Assignee: Ferro Corporation, Cleveland, OH (US)

( * ) Notice: Subject to any disclaimer, the term of this patent is extended or adjusted under 35 U.S.C. 154(b) by 168 days.

This patent is subject to a terminal disclaimer.

(21) Appl. No.: 10/552,008

(22) PCT Filed: Jun. 21, 2005

(86) PCT No.: PCT/US2005/021970
§ 371 (c)(1),
(2), (4) Date: Mar. 13, 2007

(87) PCT Pub. No.: WO2006/016981
PCT Pub. Date: Feb. 16, 2006

(65) Prior Publication Data
US 2007/0267768 A1 Nov. 22, 2007

Related U.S. Application Data

(60) Provisional application No. 60/587,303, filed on Jul. 12, 2004.

(51) Int. Cl.
*C08J 9/26* (2006.01)

(52) U.S. Cl. ............... 264/211.16; 264/211.19; 264/343; 264/177.2; 264/328.18; 264/232; 264/49; 264/344; 264/5; 264/6; 264/7; 264/8; 264/9; 264/10; 264/11; 264/12; 210/634; 210/639; 424/450; 424/484; 424/489

(58) Field of Classification Search ............. 264/211.16, 264/211.19, 343, 177.2, 328.18, 232, 49, 264/344, 61, 5–12; 977/700, 773, 779; 524/61; 210/634, 639; 424/450, 484, 489–502
See application file for complete search history.

(56) References Cited

U.S. PATENT DOCUMENTS

| | | | | |
|---|---|---|---|---|
| 5,198,115 | A | * | 3/1993 | Stalling et al. ............. 210/634 |
| 6,063,138 | A | * | 5/2000 | Hanna et al. .............. 23/295 R |
| 6,197,270 | B1 | | 3/2001 | Sonoda et al. |
| 6,447,991 | B1 | * | 9/2002 | Daitch et al. ................. 435/5 |

(Continued)

OTHER PUBLICATIONS

International Search Report for PCT/US2005/21970 mailed Oct. 12, 2006, four pages.

(Continued)

*Primary Examiner* — Christina Johnson
*Assistant Examiner* — Saeed M Huda
(74) *Attorney, Agent, or Firm* — Rankin, Hill & Clark LLP (57) ABSTRACT

The present invention provides a method of producing porous structures, particles or matrixes, which may be comprised of one or a plurality of components, an apparatus for carrying out the method and particles formed in accordance with the method. The method is particularly suitable for producing porous composite or pure particles for pharmaceutical applications. In accordance with the method, a composite comprising a material such as a pharmaceutical, a biodegradable polymers and/or a biological agent is formed. The composite must further comprise a material that is soluble in supercritical fluid. Extraction of the supercritical fluid soluble material produces porous structures, which may be in the form of particles or matrixes.

2 Claims, 5 Drawing Sheets

U.S. PATENT DOCUMENTS

| | | | |
|---|---|---|---|
| 6,670,402 | B1 | 12/2003 | Lee et al. |
| 7,083,748 | B2 | 8/2006 | Chattopadhyay et al. |
| 7,455,797 | B2 * | 11/2008 | Shekunov et al. ............... 264/5 |
| 2002/0005600 | A1 * | 1/2002 | Ma ................... 264/49 |
| 2002/0094318 | A1 * | 7/2002 | Lee et al. ................ 424/46 |
| 2004/0156911 | A1 * | 8/2004 | Chattopadhyay et al. .... 424/489 |
| 2006/0076293 | A1 | 4/2006 | Shekunov et al. |
| 2006/0138687 | A1 | 6/2006 | Shekunov et al. |

OTHER PUBLICATIONS

Uchida et al., "Preparation and Characterization of Polylactic Acid Microspheres Containing Water-Soluble Anesthetics with Small Molecular Weight," Chem. Pharm. Bull. 45(3), Mar. 1997, pp. 513-517.

Zhu et al., "Preparation and characterization of hCG-loaded polylactide or poly(lactide-co-glycolide) microspheres using a modified water-in-oil (w/o/w) emulsion solvent evaporation technique," J. Microencapsulation, 2001, vol. 18, No. 2, pp. 247-260.

Alex et al., "Encapsulation of water-soluble drugs by a modified solvent evaporation method. I. Effect of process and formulation variables on drug entrapment," J. Microencapsulation, 1990, vol. 7, No. 3, pp. 347-355.

Pistel, et al., "Effects of salt addition on the microencapsulation of proteins using W/O/W double emulsion technique," J. Microencapsulation, 2000, vol. 17, No. 4, pp. 467-483.

* cited by examiner

PRODUCTION OF POROUS MATERIALS BY SUPERCRITICAL FLUID PROCESSING

BACKGROUND OF THE INVENTION

1. Field of Invention

The present invention relates generally to a method of producing porous structures, particles or matrixes, an apparatus for carrying out the method and porous particles formed in accordance with the method.

2. Description of Related Art

Porous or hollow particles of pure pharmaceuticals and composite particles, which can also contain one or more excipients such as biodegradable polymers, are desired for various drug delivery applications. Ideally, such particles would have low bulk density, reduced inter-particle interactions and good aerosol properties making them optimal for respiratory inhalable formulations. For instance solid porous drug particles in the aerodynamic size range between 1-5 microns having a geometric volume diameter between 1 and 20 microns are required for improved delivery of therapeutic agents to the respiratory tract. Further increased interest in recent years in gene therapy and needle free administration of proteins and vaccines has also prompted the need for preparation of composite porous particles for delivery through the respiratory route. Other drug delivery applications may include the drug-encapsulated porous or hollow particles as well as implantable porous polymeric matrixes for controlled or sustained release, and bioactive scaffolds for cell growth and tissue engineering.

Conventional techniques predominantly used in the pharmaceutical industry for producing porous materials include liquid phase antisolvent precipitation, freeze-drying and bleaching of composite matrixes with water or organic solvents. Unfortunately these techniques often incur various limitations during processing, the most important of which are poor control over residual solvents, adverse liquid solvents effect on chemical and physical stability of the porous materials produced, and chemical and thermal degradation due to use of high temperature or shear.

In recent years supercritical fluids (SCFs) have been effectively used to precipitate porous particles, more specifically porous particles of biodegradable polymers and drug composites. SCFs or compressed gasses or liquids (collectively referred to here after as "SCFs") offer several advantages such as efficient extractions, mild operating conditions and clean environmentally benign processing.

The conventional supercritical fluid (SCF) techniques used for porous particle productions include the SCF antisolvent technique and its variations and the particles from expansion of SCF saturated technique. The porosity of the particles produced via both techniques is imparted due to diffusion into the atmosphere of the SCF dissolved in the biodegradable polymer matrix upon depressurization. The main disadvantage of both these techniques is that the process is limited to materials in which SCF can readily diffuse, namely a select few biodegradable polymers. In the antisolvent process, even if the SCF is readily soluble in the polymer, operating conditions must be selected such that dissolution of the SCF in the polymer does not cause plasticization of the polymer leading to melting and agglomeration of the polymer particles.

In view of the limitations of the conventional techniques, the present invention provides a new technique for producing porous structures such as particles, which can comprise only a single material such as a pure drug or can comprise a plurality of materials such as a drug and an excipient. The method offers precise control over the material bulk density, degree of porosity and pore size for various applications.

BRIEF SUMMARY OF THE INVENTION

In accordance with the method of the invention, porous materials are obtained by first forming a solid composite comprising at least a first material that is not solvent in supercritical fluid and a second material that is solvent in supercritical fluid. Supercritical fluid is then used to extract the second material from the composite to form a porous material.

The composite can be prepared using any conventional technique for producing composites. For example, the composite can be prepared by any of the following processes: melt extrusion, co-precipitation, spray drying, and lyophilization. Alternatively, the composite can also be obtained by forming an oil-in-water emulsion using an organic solution of the first material and the second material followed by liquid solvent or supercritical fluid solvent extraction of the organic solvent.

Once the composite is formed, porosity is created by SCF extraction of the second material that is soluble in the supercritical fluid. In other words, pores are formed via leaching of the second material from the composite. Pore size is controlled by changing the rate of extraction of the SCF soluble compound and/or by varying the amount of the second material in the composite. Porous structures formed in accordance with the method are free of the second material, solvents and other impurities or additives that are soluble in SCF under defined conditions of pressure and temperature.

Any suitable SCF-extraction technique known to prior art can be employed for the extraction of the SCF-soluble second material from the composite. For example the SCF-soluble second material can be extracted in a high-pressure vessel by direct contact or in an extraction column or a fluidized bed. The composite can also be suspended in a non-supercritical fluid soluble solvent such as water with or without the help of surfactants and contacted with the SCF to extract the SCF-soluble second material. Alternatively, the composite can be precipitated using known anti-solvent precipitation processes and then the pressure and/or temperature increased to extract the SCF-soluble second material from the composite.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

The first step of the method of forming porous structures according to the present invention is to form a composite comprising at least a first material that is not soluble in supercritical fluid and a second material that is soluble in supercritical fluid. The second step of the method of the invention is to extract the SCF-soluble second material from the composite to yield a porous structure, which may be a matrix or a particle.

The composite can be formed using any technique known in the prior art. The composite can be in the form of composite particles and can be formed by processes such as, for example, spray drying, crystallization, precipitation, emulsion extraction and lyophilization. The amount of the SCF-soluble second material present in the composite can be varied depending on the degree of porosity desired in the final product. Suitable compounds for use as the SCF-soluble second material include, but are not limited, lipids, waxes, polymers, sugar acetates, and fluorocarbons.

In a first embodiment of the invention, porous particles are obtained by passing SCF through a bed of composite particles comprising a first material that is not soluble in the SCF and a second material that is soluble in the SCF. The composite particles in this case can either be in a fluidized state or in the form of a packed bed depending on the SCF flow rate.

In a second embodiment of the invention, porous particles are formed by bubbling SCF through a suspension of composite particles suspended in a non-SCF soluble solvent. In some cases, surfactants may be employed to keep the composite particles suspended in the non-SCF soluble solvent.

In a third embodiment of the invention, porous matrixes are obtained by directly contacting a preformed composite matrix with SCF. In this embodiment, the extraction step can be carried out using a high-pressure vessel of arbitrary or specific shape required to produce drug delivery devices in a desired form such as, for example, disks, films and pellets.

Figure 1:
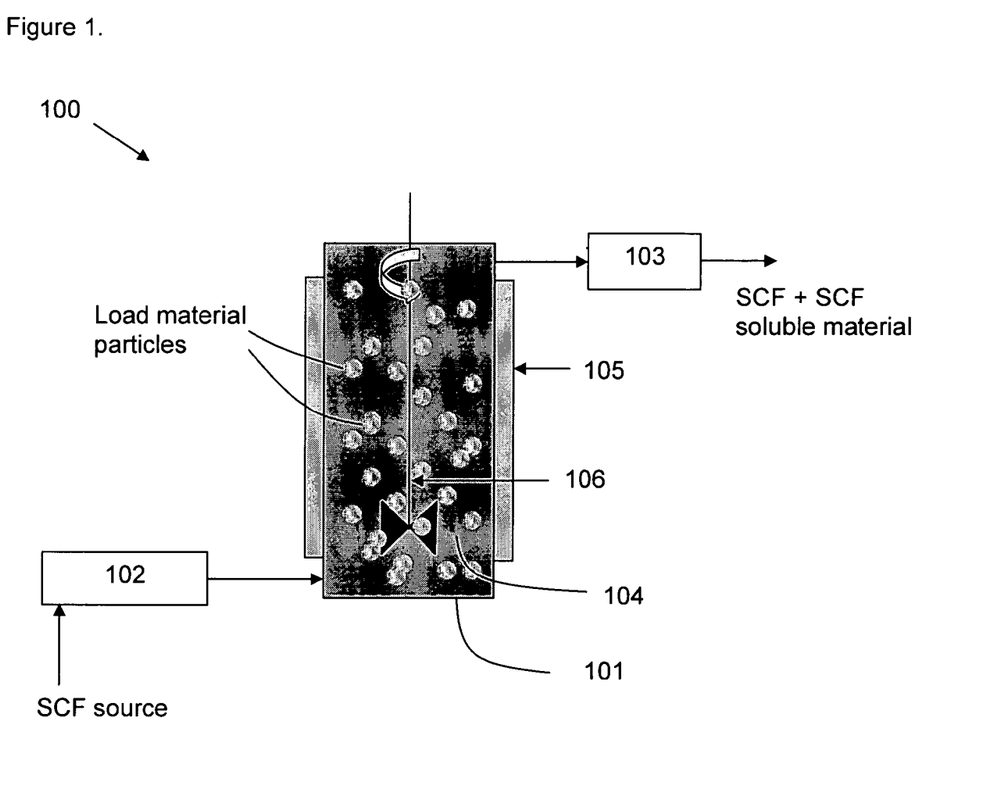
FIG. 1 is a schematic representation of an apparatus for implementing a method according to the first embodiment of the invention.

With reference to FIG. 1, which shows a schematic representation of an apparatus 100 for carrying out the first embodiment of the invention, a high-pressure extraction vessel 101, a SCF pump 102 and a backpressure regulator 103 are interconnected. The high-pressure extraction vessel 101 is preferably tubular and defines an axis, and has first and second ends that are spaced axially apart. The high-pressure extraction vessel 101 has an inner surface that defines a chamber 104. The extraction vessel has means, not shown, for accessing the interior of the vessel so as to charge the interior with a load material. The extraction vessel has a heating jacket 105 (either circulating or electrical) for heating the contents of the extraction vessel at the desired operating temperature.

The load material consists of composite particles of preferably biologically active material, for example a drug, a pharmaceutical, or a therapeutic agent and a SCF soluble material. Alternatively, the load material can include composite particles consisting of for example, medicinal agents, proteins, peptides, sugars, pigments, toxins, insecticides, viral materials, diagnostic aids, agricultural chemicals, nutritional materials, alkaloids, alkyloids, animal and/or plant extracts, dyes, explosives, polymer precursors, cosmetics, antigens, enzymes, catalysts, nucleic acids, zeolites, polymer precursors, and combinations thereof. One of the materials in the vessel must be a SCF soluble material. The load material can further include additional material(s), for example, a carrier, polymer, filler, disintegrant, binder, solubilizer, excipient, and combinations thereof along with a SCF soluble material. A preferred load material is a combination of a biologically active material, a polymer and a SCF soluble material. Preferred polymers include, for example, a polysaccharide, polyester, polyether, polyanhydride, polyglycolide (PLGA), polylactic acid (PLA), polycaprolactone (PCL), polyethylene glycol (PEG), and polypeptide. Preferred SCF soluble materials include lipids, waxes and polymers and their combinations.

The supercritical fluid pump 102 is preferably a P-200 high-pressure reciprocating pump commercially available from Thar Technologies, Inc. (Pittsburgh, Pa.). Suitable alternative pumps include diaphragm pumps and air-actuated pumps that provide a continuous flow of supercritical fluid. The high-pressure pump preferably comes factory-equipped with a burst-type rupture disc, manufactured by Fike Inc. (Blue Springs, Mo.), which is plumbed into a pressure relief system.

The supercritical fluid pump is in fluid communication with the high-pressure extraction vessel and supplies supercritical fluid to the extraction vessel. With reference to the supercritical fluid that the supercritical fluid pump supplies to the chamber, as noted hereinabove and used herein "supercritical fluid" includes not only supercritical fluid, but also compressed gas and liquefied gas, and other materials suitable, for example, to form a melt as described herein. The supercritical fluid is preferably supercritical carbon dioxide ("$CO_2$"). Suitable alternative fluids include, nitrous oxide, dimethylether, straight chain or branched C1-C6-alkanes, alkenes, fluoroform, chlorotrifluoromethane, chlorodifluoromethane, propylene, ammonia and combinations thereof. Preferred alkanes include ethane, propane, butane, isopropane, and the like. The supercritical fluid is chosen generally with reference to the ability of the supercritical fluid to extract the SCF soluble material from inside the composite particles for porous particle formation.

Disposed inside the extraction vessel is preferably a high-speed mixer 106 for mixing the contents of the extraction vessel intimately. The mixer apparatus includes a motor, a shaft extending from the motor through the second end of the mixing vessel and into the chamber, and a rotor disposed at a distal end of the shaft and located in the chamber. The mixing rate is controlled by the rotation speed and geometry (type and diameter) of the rotor. The rotor is preferably a propeller-shaped two-bladed mixer. Additional, supplemental and alternative mixing methods include both static and moving mixing devices, such as baffles, rotors, turbines, shear-mixers, ultrasonic devices, and other devices or mechanisms used to mix the contents of the mixing assembly.

Pressure inside the extraction vessel is maintained using a backpressure regulator. The backpressure regulator 103 is preferably a 26-1700-type regulator, which is commercially available from Tescom, USA (Elk River, Minn.).

For safety the extraction vessel connected with a release valve not shown in figure. The release valve is preferably a model R3A ¼" proportional pressure release valve, which is commercially available from Swagelok, Inc. (Solon, Ohio). The release valve is actuated by system pressure acting against a spring, and is capable of reseating.

Operation in accordance with the first embodiment of the invention using apparatus 100 is carried out using the following steps. First the composite particles containing the SCF soluble second material is loaded into the extraction vessel. The thermostat controls the temperature of the extractor to a predetermined and equilibrated temperature. The supercritical fluid pump supplies supercritical fluid to the extractor chamber at the first end of the extractor at a predetermined constant pressure. The SCF flows through a packed bed of composite particles or through a fluidized bed depending on its flow rate. The SCF extracts the SCF soluble second material from inside the composite particles leaving tiny pores in them. The rate of extraction of the SCF soluble second material, the amount of this material, the pressure and temperature, all can be used to control the sizes of the pores formed. Once the extraction process is complete, the SCF flow is terminated and the extraction chamber is depressurized in order to collect the porous particles formed.

Figure 2:
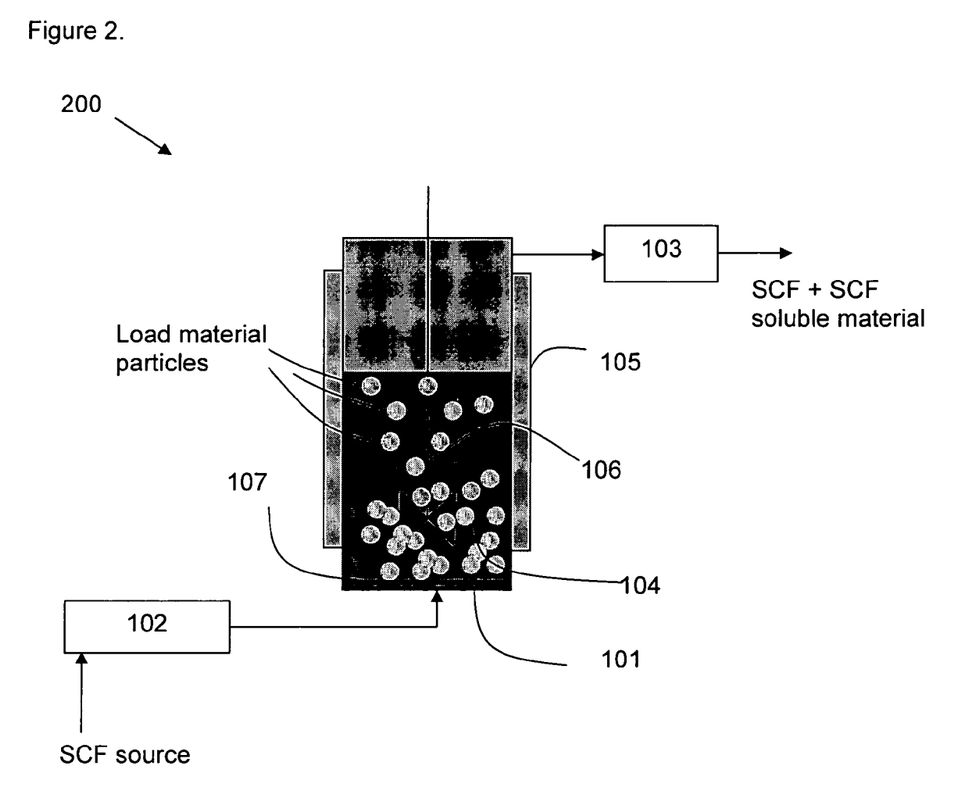
FIG. 2 is a schematic representation of an apparatus for implementing a method according to the second embodiment of the invention.

All components of the apparatus 200 shown in FIG. 2, which is used to carry out the second embodiment of the invention, are similar to the one used in the first embodiment except that disposed inside apparatus 200 is a frit 107 that breaks the SCF into a plurality of droplets inside the extraction chamber. Operation in accordance with the second embodiment of the invention using apparatus 200 is carried out using the following steps. First the composite particles containing the SCF soluble material is loaded into the extraction vessel in the form of a suspension in a non-SCF soluble solvent such as, for example, water. Surfactants are preferably used in the non-SCF soluble phase in order to stabilize the composite particles. The thermostat controls the temperature of the extractor to a predetermined and equilibrated temperature. The supercritical fluid pump supplies supercritical fluid to the extractor chamber at the first end of the extractor through a frit at a predetermined constant pressure. The SCF flows through a composite particle suspension in the form of fine droplets. The SCF extracts the SCF soluble second material from inside the composite particles leaving tiny pores in them. The rate of extraction of the SCF soluble second material, the amount of this material, the pressure and temperature, all can be used to control the sizes of the pores formed. Once the extraction process is complete, the SCF flow is terminated and the extraction chamber is depressurized in order to collect the porous particle suspension.

Figure 3:
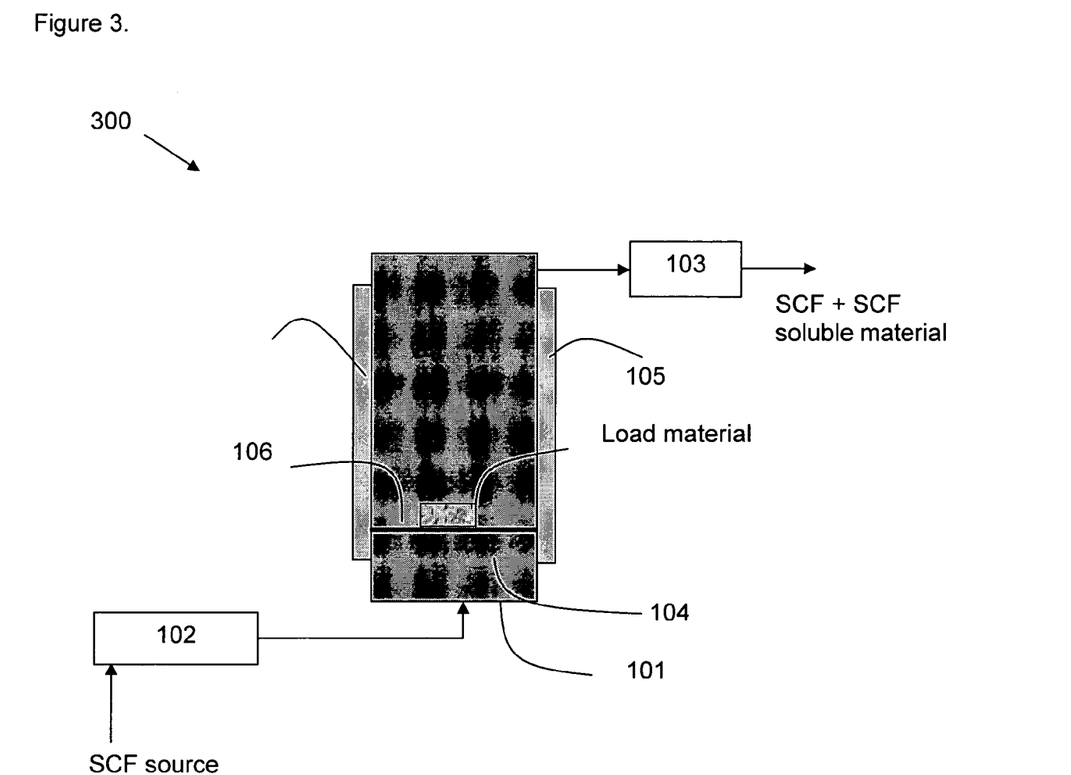
FIG. 3 is a schematic representation of an apparatus for implementing a method according to the third embodiment of the invention.

The components of the apparatus 300 shown in FIG. 3, which is used to carry out the third embodiment of the invention, consists of many components similar to the one used in the first and second embodiment. However the mixing device is usually not provided for extraction of the SCF-soluble second compound from the polymer matrix. Instead, the polymer matrix is placed inside the extraction vessel and SCF is allowed to diffuse within the matrix to extract the SCF-soluble compounds.

Operation in accordance with the third embodiment of the invention using apparatus 300 is carried out using the following steps. First the composite material in a preformed shaped is placed inside the extraction vessel. The vessel may be of different size and shape compatible with the specific shape of the polymer matrix. The thermostat controls the temperature of the extractor to a predetermined and equilibrated temperature. The supercritical fluid pump supplies supercritical fluid to the extractor chamber at a predetermined constant pressure. The SCF flows through the extraction camber and diffuses into the composite matrix. The SCF extracts the SCF soluble second material from inside the matrix thereby creating pores. The rate of extraction of the SCF soluble second material, the amount of this material, the pressure and temperature, all can be used to control the sizes of the pores formed. Once the extraction process is complete, the SCF flow is terminated and the extraction chamber is depressurized in order to collect the porous matrix.

The following examples are intended only to illustrate the invention and should not be construed as imposing limitations upon the claims.

EXAMPLE 1

3.0 grams of poly(lactide/glycolide) (PLGA) and 1.5 g of lipid (Gelucire 50/13) were added to 60 grams of dichloromethane (DCM) in order to form an organic solution. The organic solution was added into 160 grams of an aqueous solution of poly vinyl pyrolidone (PVP, 2% w/w) in order to form a mixture. The mixture was dispersed or emulsified using a dispersator for about 2 minutes at 2000 rpm to form a crude O/W emulsion. The crude O/W emulsion was then homogenized using a homogenizer commercially available from Microfluidics, Inc. (Newton, Mass.) at 5,000 psi pressure and three passes to form a final O/W emulsion.

Precipitation of particles was carried out by supercritical fluid extraction of the DCM from the final O/W emulsion using the apparatus described in Example 1(a) of Chattopadhyay et al., U.S. Pub. App. 2004/0026319 A1, which is hereby incorporated by reference in its entirety. The extraction conditions were 80 bar pressure and 35° C. temperature. The flow rate of supercritical $CO_2$ employed was 30 g/min and the flow rate of final O/W emulsion was 3 ml/min. Extraction of DCM from the emulsion resulted in precipitation of composite particles comprising PLGA and lipid, which were in the form of a PVP stabilized aqueous suspension.

The PVP stabilized aqueous suspension of composite particles was loaded into an extraction chamber of an apparatus such as shown in FIG. 2. The extraction chamber temperature was maintained at 45° C. Supercritical $CO_2$ was made to flow through the extraction chamber and through the particle suspension at a 0.5 ml/min and 150-bar pressure to extract the Gelucire 50/13 lipid from the composite particles. After complete extraction of Gelucire 50/13 from the composite particles, the supercritical $CO_2$ flow was terminated and the extraction chamber was depressurized. The resulting aqueous suspension of porous particles thus formed was collected and taken for analysis.

Figure 4:
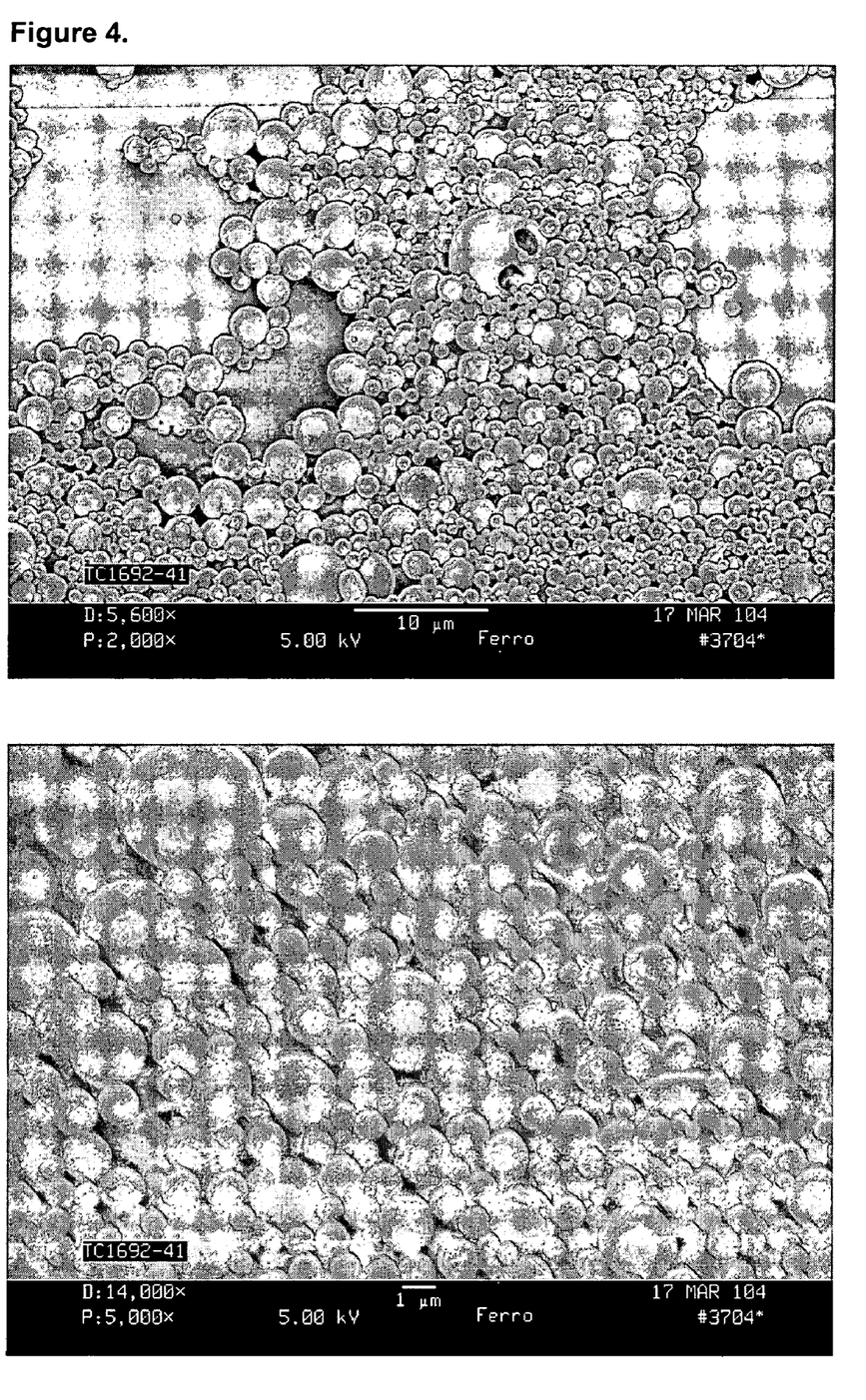
FIG. 4 is an SEM micrograph of non-porous composite particles.
Figure 5:
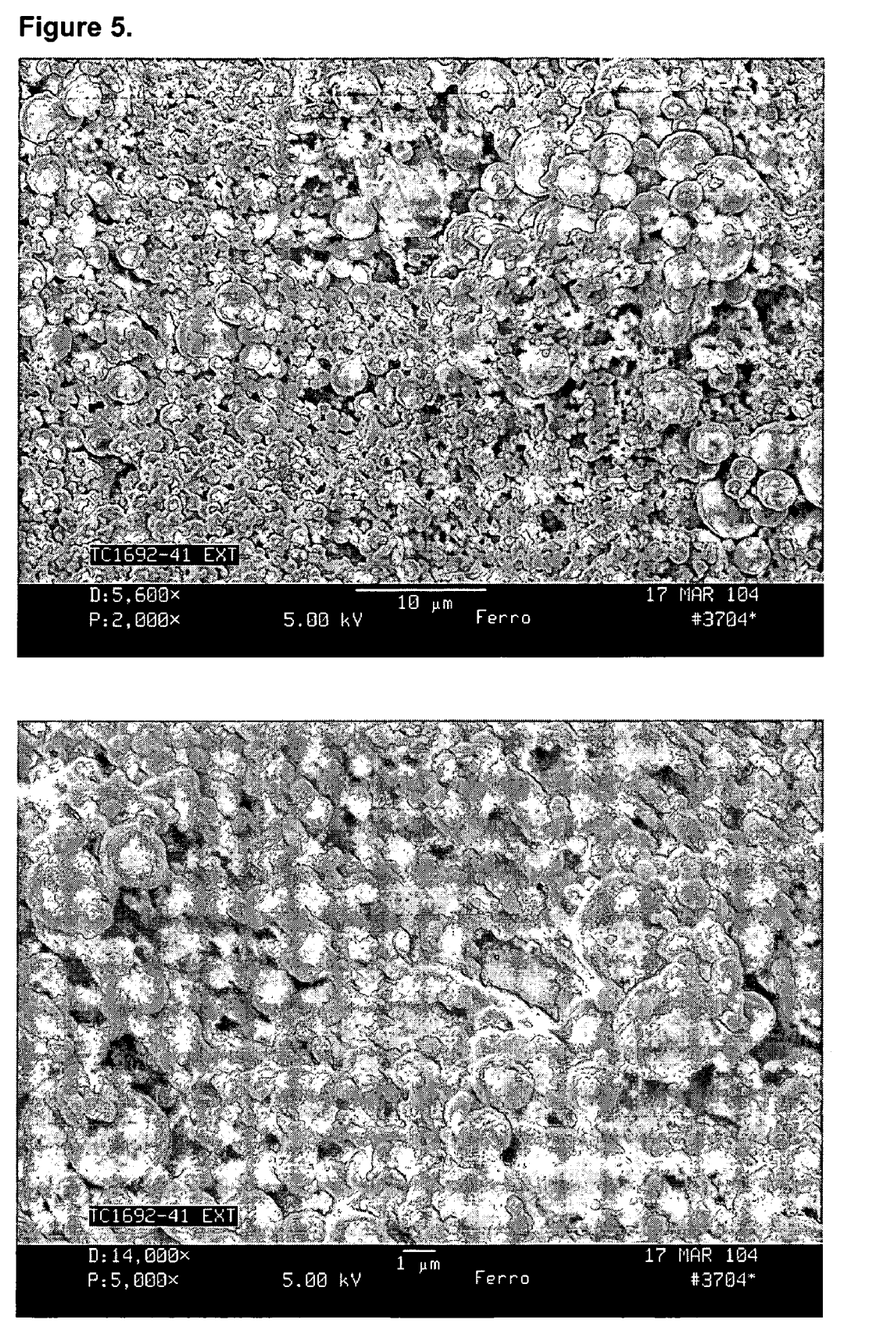
FIG. 5 is an SEM micrograph of porous particles according to the invention.

Analysis of the particles was carried out using Scanning Electron microscopy (SEM). FIG. 4 is an SEM micrograph of the composite particles before extraction of the lipid using supercritical $CO_2$. FIG. 5 is an SEM micrograph of the porous particles after the lipid had been extracted. FIGS. 4 and 5 illustrate the change in the surface morphology of the particles due to extraction of the SCF soluble material and due to the introduction of pores.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of forming porous particles, the method comprising:

providing an aqueous suspension of composite particles, the composite particles comprising at least a first material that is not soluble in supercritical carbon dioxide and a second material that is soluble in supercritical carbon dioxide, wherein the first material is a solid selected from the group consisting of pharmaceuticals, biodegradable polymers, biological agents and combinations of two or more thereof, and the second material is a solid selected from the group consisting of lipids, waxes, polymers, sugar acetates and fluorocarbons; and bubbling supercritical carbon dioxide through the aqueous suspension of composite particles to extract the second material from the composite particles and thus form an aqueous suspension of porous particles comprising the first material suspended in water, the porous particles have an aerodynamic size range of from about 0.5 to about 5 microns and a geometric volume diameter of from about 1 to about 20 microns.

2. A method of forming porous particles, the method comprising:
provinding a supercritical fluid;
providing a first material that is not soluble in the supercritical fluid, wherein the first material is a solid selected from the group consisting of pharmaceuticals, biodegradable polymers, biological agents and combinations of two or more thereof, and;
providing a second material that is soluble in the supercritical fluid, wherein the second material is a solid selected from the group consisting of lipids, waxes, polymers, sugar acetates and fluorocarbons;
contacting the first material and the second material together to form composite particles;
dispersing the composite particles in a solvent that is not soluble in the supercritical fluid to form a suspension of composite particles; and
bubbling the supercritical fluid through the suspension of composite particles to extract the second material from the composite particles and thus form a suspension of porous particles comprising the first material, wherein the porous particles have an aerodynamic size range of from about 0.5 to about 5 microns and a geometric volume diameter of from about 1 to about 20 microns.

* * * * *